United States Patent [19]

Forster et al.

[11] 4,267,410

[45] May 12, 1981

[54] PROSTHESIS

[75] Inventors: Ian C. Forster, Hawthorn; James F. Patrick, North Melbourne; Yit C. Tong, Burwood; Raymond C. Black, Carlton; Graeme M. Clark, Eltham, all of Australia

[73] Assignee: The University of Melbourne, Parkville, Australia

[21] Appl. No.: 956,795

[22] Filed: Nov. 1, 1978

[30] Foreign Application Priority Data

Nov. 3, 1977 [AU] Australia .............................. PD2291

[51] Int. Cl.³ .......................................... H04R 25/00
[52] U.S. Cl. .......................... 179/107 BC; 179/100 R
[58] Field of Search ........ 179/107 R, 107 BC, 107 E, 179/107 FD; 3/1.1; 340/407

[56] References Cited

U.S. PATENT DOCUMENTS

| 3,449,768 | 1/1969 | Doyle | 3/1 |
| 3,727,616 | 4/1973 | Lenzkes | 128/419 E |
| 3,752,939 | 8/1973 | Bartl | 179/107 R |
| 4,049,004 | 9/1977 | Walters | 128/419 PG |
| 4,063,048 | 12/1977 | Kissiah, Jr. | 179/107 R |

OTHER PUBLICATIONS

"Data processing, LSI will help to bring sight to the blind", Electronics Magazine, 1/24/74, pp. 81–86.
"A CMOS Implantable Multielectrode Auditory Stimulator for the Deaf", Gheewala et al., IEEE Jour. of Solid-State Circuits, Dec. 1975.

Primary Examiner—Vincent P. Canney
Attorney, Agent, or Firm—J. Harold Nissen

[57] ABSTRACT

A prosthesis and specifically an aural prosthesis which includes an implantable component which is in connection with means which can selectively stimulate neural endings the component being arranged to receive a signal from an extension component which converts a parameter into a transmittable form and which includes a transmitter, the signal from the transmitter received by the implanted component which resolves the signal into groups of two components which can selectively stimulate the neural endings, the stimulation to each ending being independent to stimulation of each other neural ending in both intensity and phase.

5 Claims, 12 Drawing Figures

THE OVERALL PROSTHETIC SYSTEM.

FIG. 1. THE OVERALL PROSTHETIC SYSTEM.

FIG. 2. - DATA TRAIN COMPOSITION

FIG. 3 — POWER SUPPLY & DATA DEMODULATOR

SYNG & CLOCK SEPARATION

FIG. 3A. RECEIVER

FIG. 4 — BASIC ARRANGEMENT OF CHANNEL CONTROL (CHANNEL 17 SHOWN)

FIG. 5. STIMULATION TIMING STRUCTURE (a) ALLOWABLE STIMULUS TIMES FOR ANY ONE CHANNEL (b) STIMULUS TIMING PATTERN

FIG. 6. OUTPUT AND STIMULATION

PROSTHESIS

This invention relates to improvements in prostheses and, in particular, in improvements to hearing prostheses.

Some persons possess sensory deafness in which condition they cannot hear but in which there is no damage to the sensory neural endings in the cochlea or inner ear.

If these neural endings could be stimulated, a sensation of hearing would be received at the brain and if the stimulation could be controlled in accordance with a particular audio sound then, "hearing" could be effected.

Similarly, where a person is suffering blindness, which is also due to a sensory fault, it is possible to stimulate the neural endings of the optic nerve so that the person can "see" and, depending on the control of such stimulation, a person may in fact see what is around him.

Further, there are conditions where certain motor functions of the body are impaired and it has been shown that these can be aided by locating electrodes to a position adjacent a nerve ending causing stimulation of that nerve and affect its associated muscle. Such arrangements are impracticable but should the control for the stimulation be implanted this could be of benefit. Even further, could several nerves be stimulated from one control system with the stimulation being independent in all ways, overall control could be achieved. A feed back arrangement could be provided to itself initiate operation of various other functions. If so, for example, the control and use of artificial limbs could be greatly improved.

It is an object of the invention to provide a prosthesis whereby nerve endings can be selectively stimulated in order to permit a patient to obtain an effect similar to the stimulation of such nerves under normal conditions.

A more specific object is to provide a hearing prosthesis whereby a sound external to a person can be used as a basis for the formation of stimuli which act on his sensory neural endings to provide an indication of the sound.

The invention includes a prosthesis including at least two parts, one of which is adapted to be located exteriorly of the body and which is arranged to convert a parameter into a form suitable for transmission and which includes a transmitter and a second part which is located within the body and which is adapted to receive a signal transmitted from the first part and to convert this into at least two signals which are adapted to provide selective stimulation to neural endings, the signals and thus the stimulation being completely independent in intensity, frequency and phase.

Where the prosthesis is to be used as a hearing prosthesis, the first part comprises a transmitter adapted to receive at least two channels of information each derived from an audio signal input, each channel including the necessary information relative to the input signal, by means of which transmitter this information is transmitted to the second part, the second part including a demodulator for the material and decoding means whereby the signals can be separated into different channels and from these channels be used to effect stimulation by means of electrodes of particular neural endings.

There may be any required number of channels which are restricted only to the number of different electrodes which can be implanted in the cochlea, but we have found that the optimum number is of the order of fifteen. Any greater number, it appears, causes interaction of the signal stimulation. The lesser the number used, particularly less than ten, so the effectiveness of the stimulation decreases.

We believe that, with reference to the current theories of hearing, the place theory of frequency coding is more important than the volley theory, which was previously considered relevant, and in the place theory the frequency of sound heard is dependant on the excitation of the neural endings spaced along the cochlea and thus "sound" can be heard by selective excitation of the neural endings at different spacings along the cochlea.

In applications other than the auditory field, a very much larger number of channels can be used as the working area may be greater and the implant size becomes less relevant.

The information from the transmitter gathered by the demodulator can effectively be comprised of two components per channel. The amplitude of the stimulus current provides an indication of intensity and the time of stimulation relative to an external time reference, which is a phase control.

Preferably, the transmitter and the demodulator are so arranged that the demodulator can make use of the carrier signal from the transmitter to provide power for the second part of the prosthesis.

In one form of the invention both the information signals and the power signals are transmitted on a single carrier. Where frequency shift keying (FSK) is used this is quite satisfactory as the carrier envelope is constant but where pulse code modulation (PCM) is used this is less satisfactory as the envelope varies with time and the demodulator would require larger filter components to obtain a constant supply voltage, depending upon the frequency of transmission. In another form two different carrier frequencies are used, one of these frequencies carries the information, the other the power for the second part of the prosthesis.

Before describing particular forms of prosthesis, which will be directed to an audio prosthesis, some consideration must be given to the maximum possible size of the second part of the prosthesis. This has to be located subcutaneously in the mastoid bone behind the external ear structure, and there is therefore a very limited space in which this can be located.

We decided that the way in which the second part is manufactured should be by the use of thick film micro circuit techniques and we have found that by using ceramic substrates which are approximately 25 mm by 15 mm we can, by the use of four substrates provide fifteen channels. The actual location or order of the various circuit components on these substrates will be described later.

In order that the invention may be more readily understood, we shall describe, by way of example of the application of the invention to hearing, particular forms of prosthesis made in accordance with the invention in relation to the accompanying drawings in which.

Figure 1:
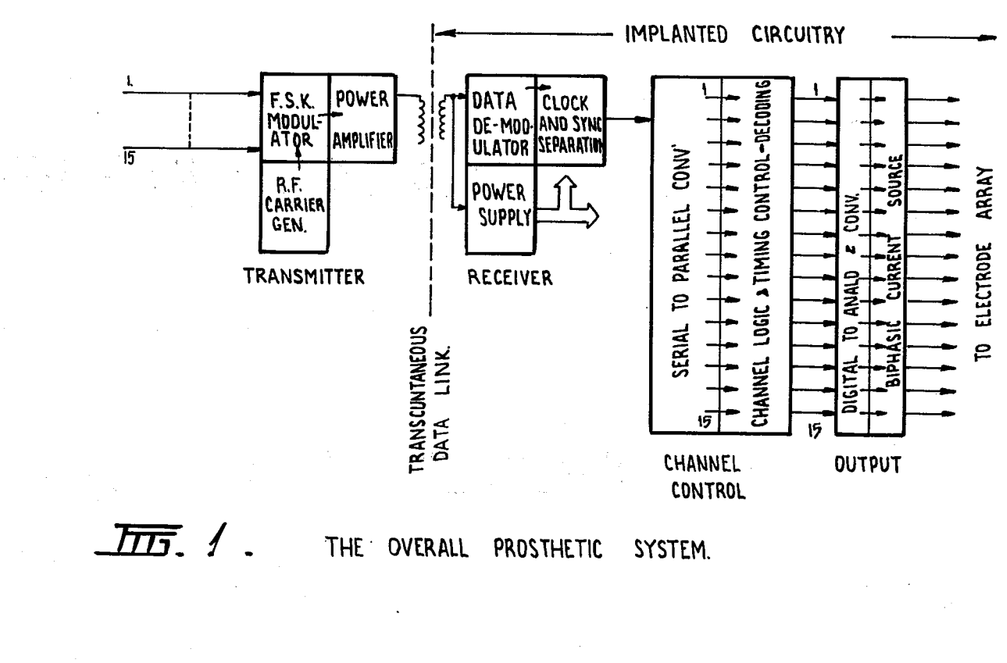
FIG. 1 is a block diagram of one form of the system as a whole, the system being a fifteen channel system.

From the block diagram of FIG. 1, it can be seen that the prosthesis comprises four basic sections which are:
(i) Transmitter
(ii) Receiver
(iii) Channel Decoder and Control
(iv) Output Section (i) which comprises the first part is located outside the body of the subject, whilst the remaining sections (ii), (iii) and (iv), which comprise the second part, are located subcutaneously in the mastoid bone behind the external ear structure.

For the signal we have chosen two stimulus parameters for this prosthetic system although it is to be understood that these could be varied. Those chosen are stimulus intensity (in this case the stimulus intensity variable is current) and the phase of stimulation relative to other channels, or an external time reference. This latter parameter could also be interpreted as frequency of stimulation for a particular channel. It should be noted that using these prostheses the actual duration of stimulation is fixed and cannot be altered.

We have also decided to use fifteen channels of digital information which are time division multiplexed to form a serial digital data train (i.e. parallel to serial data conversion) to simplify transcutaneous transmission of the data and it is this train which is the transmitter input.

Transmitter

This section provides the necessary interface between its input and the implanted circuitry. The transmitter consists of a radio frequency (RF) carrier generator which is modulated in the frequency shift keying (FSK) mode by the serial digital data train, the transmitter input. The modulated carrier drives a power amplifier with sufficient power output to couple energy transcutaneously for powering the implanted circuitry of the second part as well as activating the data demodulation circuitry. This energy will be coupled via an inductive field to the receiver inductor implanted in the mastoid bone cavity.

The Receiver

The receiver consists of three subsections viz:
(i) Power Supply
(ii) Data Demodulator
(iii) Clock and sync. separation.

Subsections (i) and (ii) derive their input from the receiver inductor, which forms part of a resonant circuit, to achieve maximal power transfer transcutaneously.

The power supply converts the RF carrier into the fixed voltage levels required for the operation of the implanted decoding, data processing and stimulation circuitry. The data demodulator demodulates the carrier and recovers the original digital data train.

The clock and sync. separator separates the synchronizing information and data from the serial data train and generates several master control clocks for the operation of the channel control circuitry.

Channel Decoder and Control

This section firstly performs a serial to parallel data conversion on the recovered data train, and this data is applied to the appropriate channel control network. The data for each channel is also divided into phase bits and analog (intensity) bits. The former determine the exact time at which the particular channel will stimulate; the latter determine the stimulus level for that time.

Output

The output of the channel control section for each of the fifteen channels are firstly the analog bits which are the input to a digital to analog converter (DAC) and secondly a control line necessary for switching in the appropriate electrode. The output of the DAC is an analog voltage which drives a biphasic current source, the output of which is applied to the electrode for that channel.

We shall now describe more fully, the operation of many of the components of the system without individually describing the particular electronic arrangements.

Figure 2:
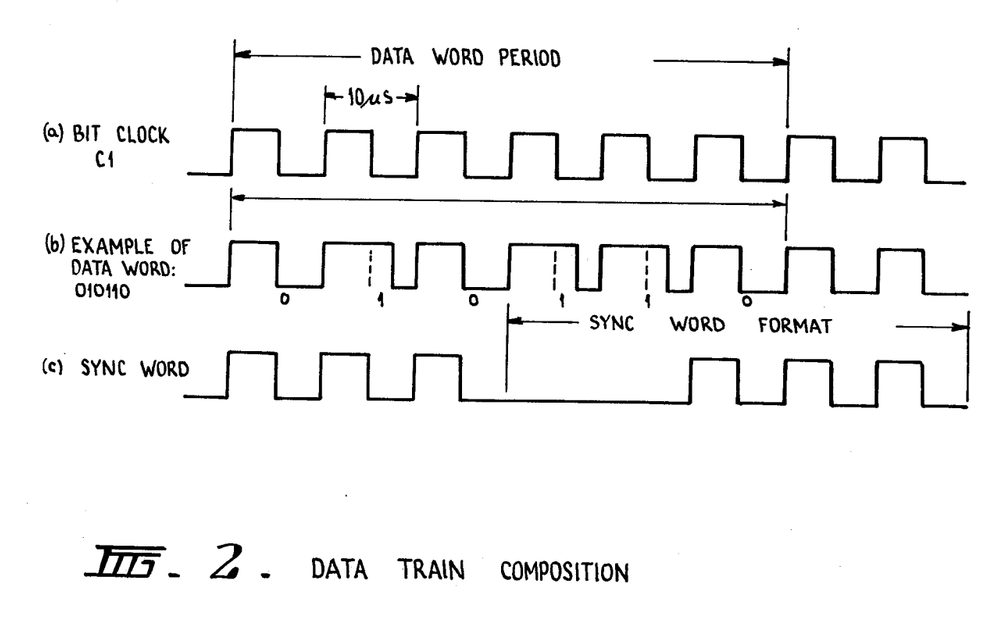
FIG. 2 shows a data train composition which is effectively the output of the data generator to be fed to the transmitter.

FIG. 2 shows the composition of the data train. It consists of a basis 10 $\mu$s clock, C1 (FIG. 2a), known as the BIT CLOCK. Each word (corresponding to the information for each channel) is six bits long; the first three bits being the analog bits, the second three being phase bits. Consequently there are eight possible times of stimulation and seven possible stimulation levels (000 corresponding to no stimulation).

Data bits are logically OR'd with the 10 $\mu$s clock train such that logical "1" data bit extends the length of the C1 pulse by approximately 2.5 $\mu$s, whereas the logical "0" data bit has no effect. FIG. 2b shows the resulting data train for:
 010 being entered for analog data
 110 being entered for phase data.

There are fifteen channels, and thus fifteen words in each frame (or sequence) of serial data.

Between frames there is a so called SYNC WORD (FIG. 2c) of 60 $\mu$s in length (equal to the channel word length). Thus the total frame cycle time is 960 $\mu$s. The sync. word appears as a time gap equal to two C1 clock intervals, followed by logic 0000 of data (i.e. four C1 clock pulses.

Although the form of this data train is valuable for the understanding of the operation of the invention, the train form can be varied and the generator of the train is not part of the invention.

Transmitter

At the present time the most satisfactory form of transmitter has an RF carrier generated by two crystal oscillators, one operating at 10.7 MHz and the other approximately 1 MHz higher. The input to the power amplifier stage is switched between these oscillators (with suitable buffering) depending on the logic state of the input data sequence.

The coupling on the outside of the skin is via an inductor wound inside a high frequency ferrite pot core section approximately 14 mm in diameter. This affords maximal coupling as well as shielding of radiation.

Receiver

Figure 3:
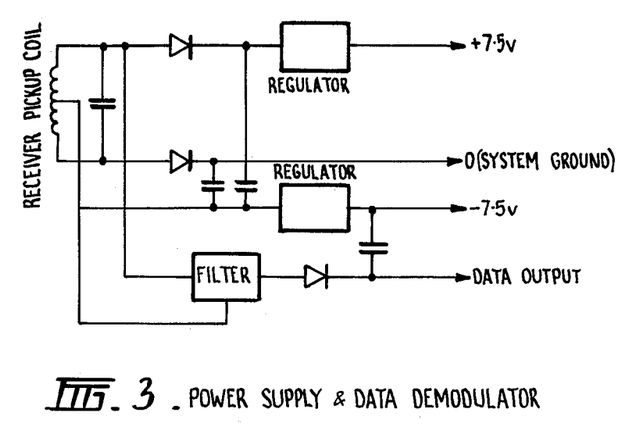
FIGS. 3 and 3a are block diagrams of the receiver.

FIG. 3 shows in block diagram form the details of the receiver's three subsections as outlined previously. The implanted receiver coil is either wound on a ferrite core former to achieve maximal coupling; or it may be a thick film coil. The latter configuration is more desirable when considering the volume limitations of the implant. This coil is resonated with a capacitor at approximately 11.2 MHz. In order to demodulate the FSK signal we employ a 10.7 MHz wideband ceramic filter to separate the two frequencies. The bandwidth of this filter is the limiting factor in determining the bit rate of the system.

Power for the implanted electronics is derived from the resonant circuit by using a half wave rectifier with capacitative filter and voltage limiting circuitry.

The preferred D.C. voltage rails for the implanted circuitry are +7.5, and −7.5 V. These also correspond to logic "1" and logic "0" levels respectively.

We prefer, in order to achieve minimum power consumption, to use the CMOS logic family for the digital data processing in the implant. The use of this logic family also places less demands on power supply filtering.

The choice of power supply rails which are bipolar with respect to the implant ground was necessitated by the desirability of having a biphasic current output, and digital to analog conversion. By using this configuration the total number of power supply bus lines are minimized.

The biphasic current output for stimulation is selected as the preferred electrodes, which are not part of this invention, used are platinum electrodes and it has been found that long term stimulation at high current density can lead to electrolysis with the production of toxic substances and loss of metal from the anode.

It has been found that such electrolysis is minimized by using biphasic current and is still further minimized if the first phase is negative relative to ground. There are on some occasions some reasons to have the first phase positive with respect to ground and these will be discussed later herein.

Figure 3A:
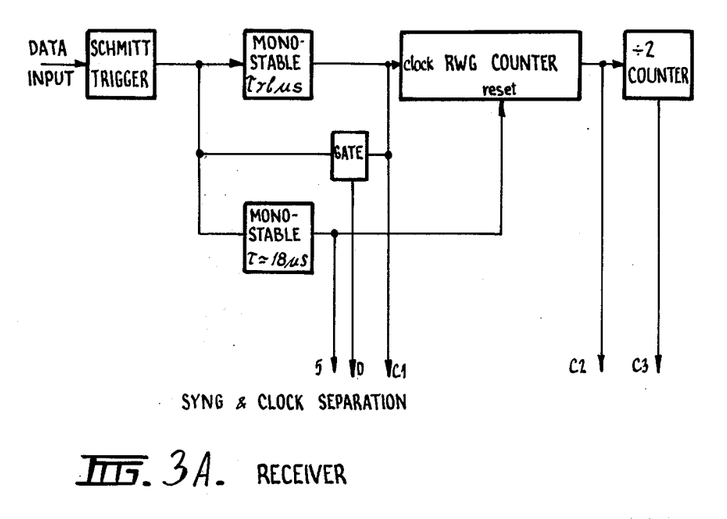

The clock and sync separation is shown in FIG. 3a and as can be seen from FIG. 3, the output of the demodulator filter is rectified and filtered and after squaring by a Schmitt trigger appears as a delayed replica of the original data train.

From this data train, all the master control clocks and synchronizing information are derived. The bit clock C1 (period 10 $\mu$s) is derived from the output of a monostable of period 6 $\mu$s, and triggered on the leading edge of the data train. The actual data bits (D) are obtained by logically NOR'ing C1 with the inverted data train: A six stage ring counter is used to derive the STIM WORD clock C2 (period 60 $\mu$s). Clock C2 is divided by two to form a PHASE CLOCK C3 with a period of 120 $\mu$s.

The sync. word is detected by another monostable which is adjusted such that it resets itself only during the bit clock gap in the data train.

Channel Control

Figure 4:
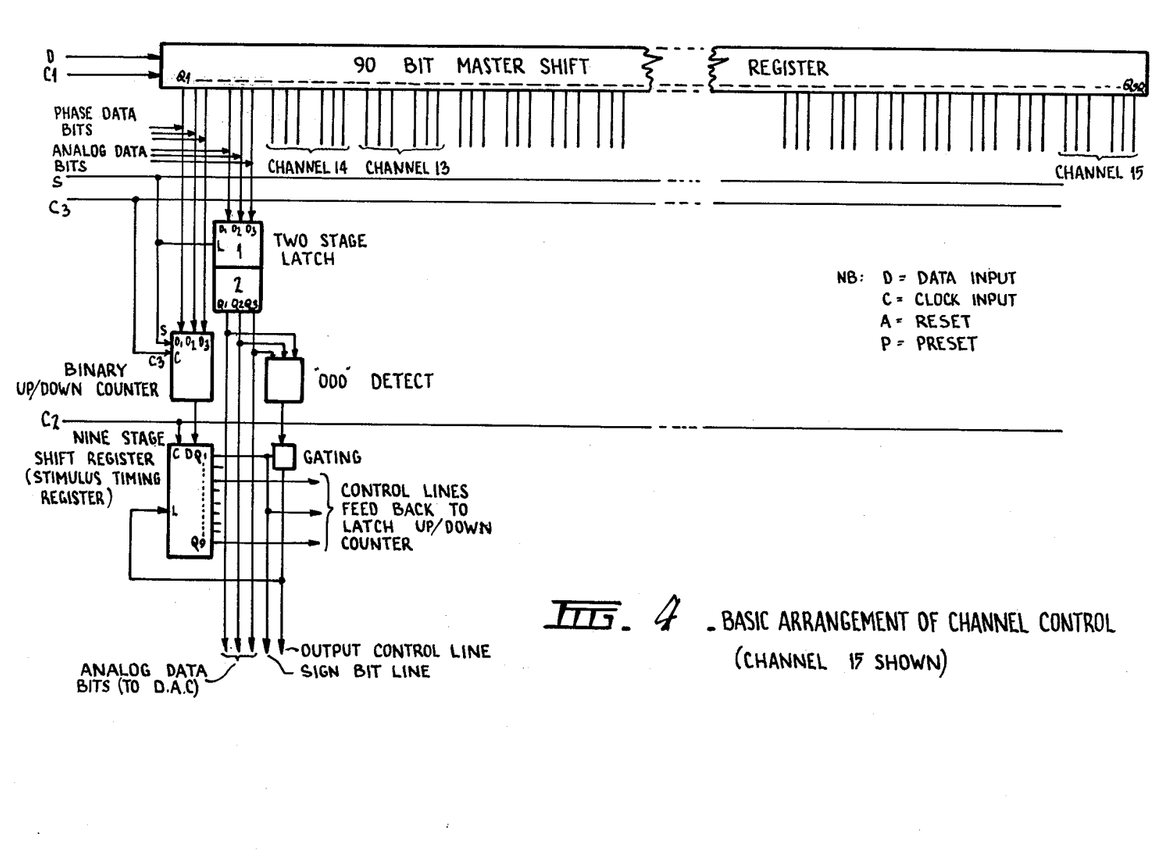
FIG. 4 is a basic arrangement of the channel control showing channel fifteen.

FIG. 4 shows a block diagram of the channel control system.

Data train D is loaded into a 90 bit serial in/parallel out master shift register in synchrony with clock C1. This data is then loaded into the appropriate channel registers when the sync pulse (signifying the end of the frame) appears. Subsequently data is clocked out of the master shift register as the next frame of data is entered. It can be seen that data can only be updated every 960 $\mu$s. Thus the maximum steady state frequency of stimulation is approximately 1.04 kHz—the instantaneous frequency can however be greater than this as will be seen later.

The first three bits in any one channel word (analog bits) are loaded into a two stage storage latch the operation of which will be indicated below. The second three bits in any channel word (phase bits) are loaded into the preset inputs of a binary up/down counter which is clocked by the phase clock C3. The leading edge of this clock represents times during the 960 $\mu$s frame when stimulation can occur for a given channel. There are eight times for a 960 $\mu$s frame corresponding to the three bits of phase data.

Figure 5:
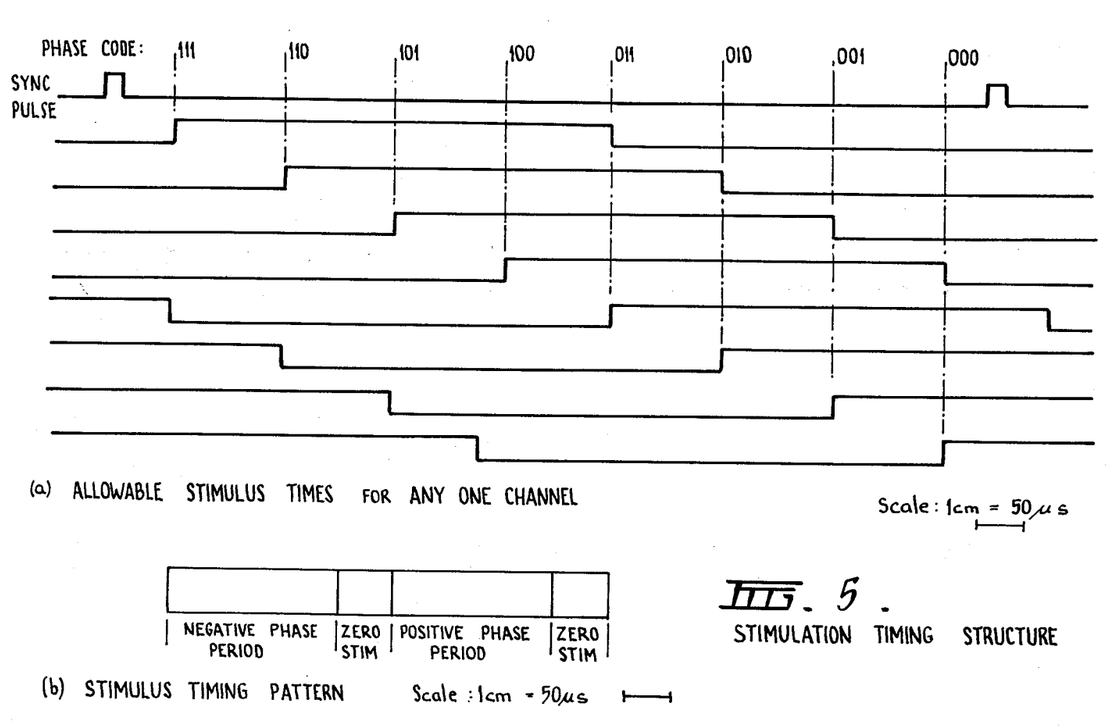
FIG. 5 is a graph showing the stimulation timing structure.

Thus, when the counter reaches the end of its count from the preset data state, the stimulus cycle begins by entering a logic "1" serially into a nine stage shift register which is clocked by stim clock, C2. The outputs of this stimulus timing register gate the analog bits into the DAC and a fourth bit is also generated for controlling the sign of the DAC output (and thus the phase of the output current). The stimulation cycle is thus made up of 60 $\mu$s quanta (C2). The positive and negative stimulus current phases are 180 $\mu$s in length with a 60 $\mu$s period of zero current flow between phases and at the end of a cycle. FIG. 5a shows the allowable stimulus times during a frame for any one channel; and FIG. 5b shows the stimulation timing pattern.

It can be seen from FIG. 5a, that under some conditions, the stimulation cycle may not have been completed by the end of the frame and hence at the instant of loading of new data. In order to avoid data in the previous frame being lost:

(1) analog data is stored in a buffer latch the state of which cannot change until stimulation is complete.
(2) data cannot be entered into the stimulus timing register (and thus a new stimulation cycle begins), until 120 $\mu$s after the previous cycle has finished. This prevents continuous stimulation of channel which could result in undesirable assymetrical current stimulation.

In order to reset the stimulus timing shift register and other latches, a logic "000" for the three bits of analog data is detected, and since this implies no stimulation for that frame, reset of various latches and registers can occur.

Output

Figure 6:
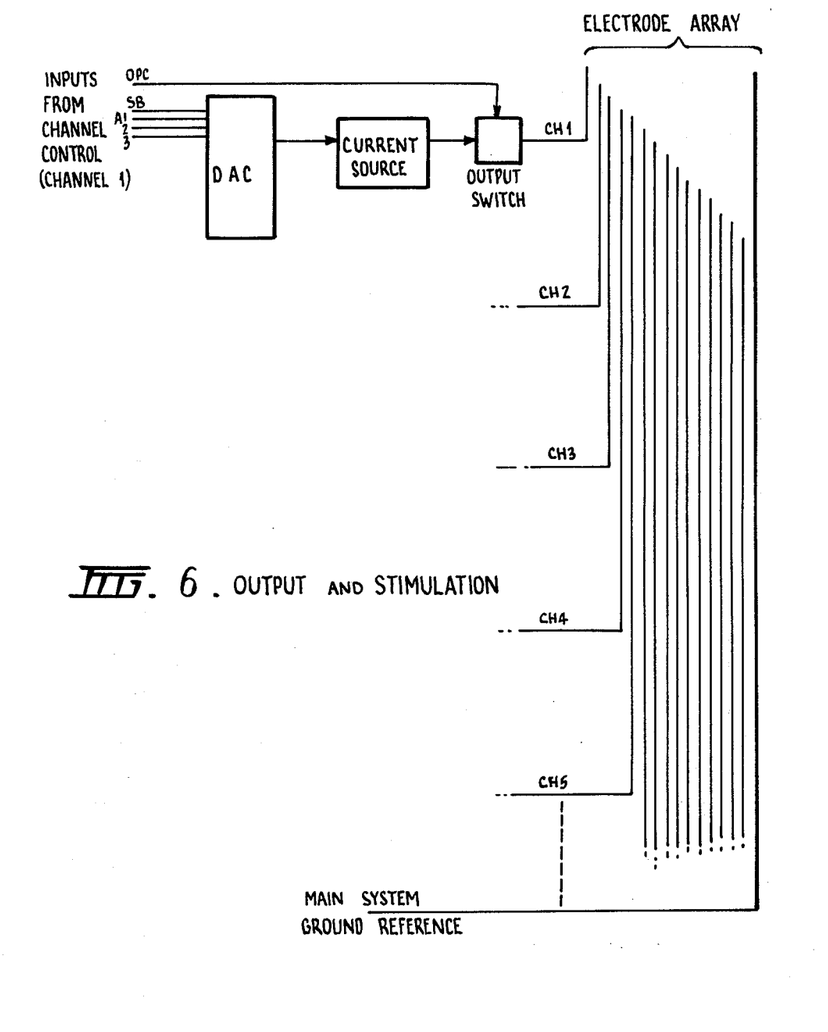
FIG. 6 shows the output of stimulation circuits.
Figure 7:
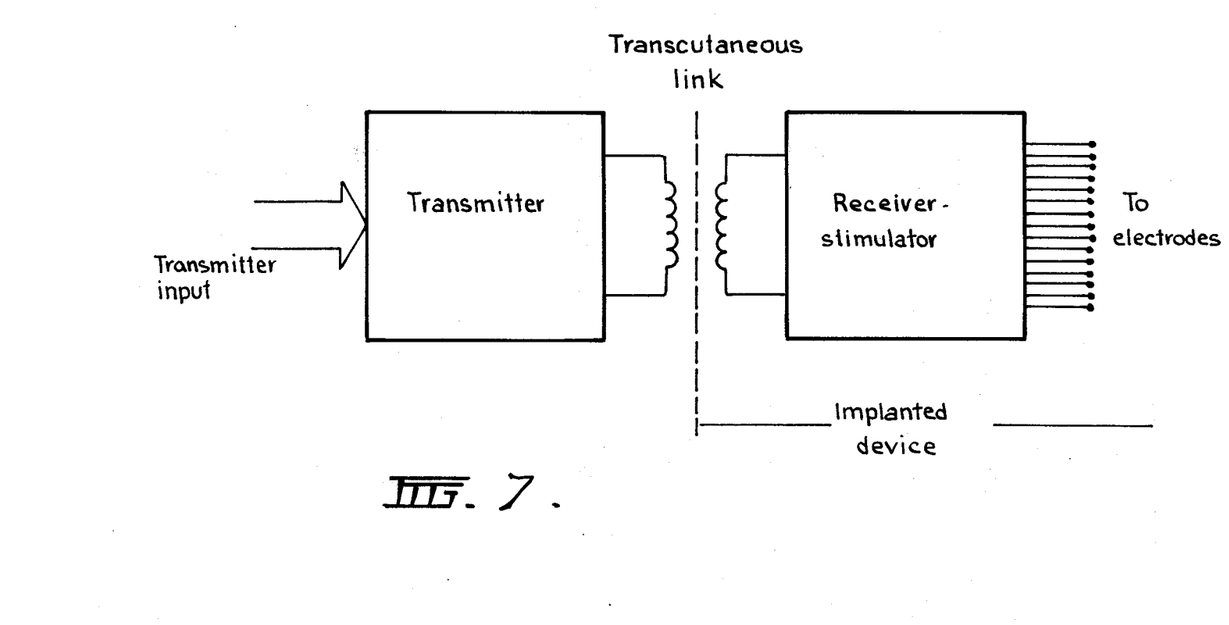
FIG. 7 is a simplified block diagram of a second form of prosthesis.

A block diagram of the output section is shown in FIG. 6.

The three analog data bits are loaded into a DAC according to the stimulus timing format shown in FIG. 5a. In order to change the sign of the DAC output symmetrically, the sign bit output generated by the stimulus timing register controls the sign of the DAC reference voltage. The DAC output voltage drives a voltage controlled current source realised using an operational amplifier with both positive and negative feedback.

The stimulus current varies from zero to 1.05 $\mu$A in 7 quanta of 150 $\mu$A corresponding to the possible states of the analog data bits.

When a channel electrode is not being stimulated the electrode is electrically isolated from the constant current source to ensure current sinking occurs only at the electrode array reference electrode. This control is effected by the output control line from the channel control circuitry.

Using substrates as previously mentioned for the second part of the circuitry, we find that the first substrate, substrate A, can contain the receiver components, the demodulation, power supply, sync and clock separation.

Substrate B can include channel controls of channels 1 to 4, substrate C channel controls of channels 5 to 8, substrate D channel controls of channels 9 to 12 and substrate E channel controls channels 13 to 15.

The sixth substrate, substrate F, comprises the output and stimulation circuitry for all channels 1 to 15.

The connection of the electrodes to the second part of the circuitry may be in any way but, because of the increased likelihood of nerve damage if electrodes have to be removed and replaced, we prefer to use a form of connector whereby, should some fault develop in the electronics, the second part can be removed without displacing the electrodes.

The prosthesis as illustrated in FIGS. 7 to 11 is a modified form of the prosthesis described hereinbefore and is generally very similar thereto. It has, as can be seen from FIG. 8, means to feed a serial signal to a transmitter, the transmitter being external of the body and transmits a signal to a receiver-stimulator which is implanted, as in the previous embodiment, in the mastoid bone. The new form of prosthesis does differ from the previous form, as can be seen from FIG. 8, the block diagram of the transmitter, in that instead of having a single carrier for both the power for the implant and the information there are two carriers, the power carrier being at 112 KHz and the data link is 10.752 MHz. We have adopted this arrangement as we find that the lower frequency enables better transfer of power through tissues whereas the higher frequency permits the data transfer to be effectively wide banded.

Figure 8:
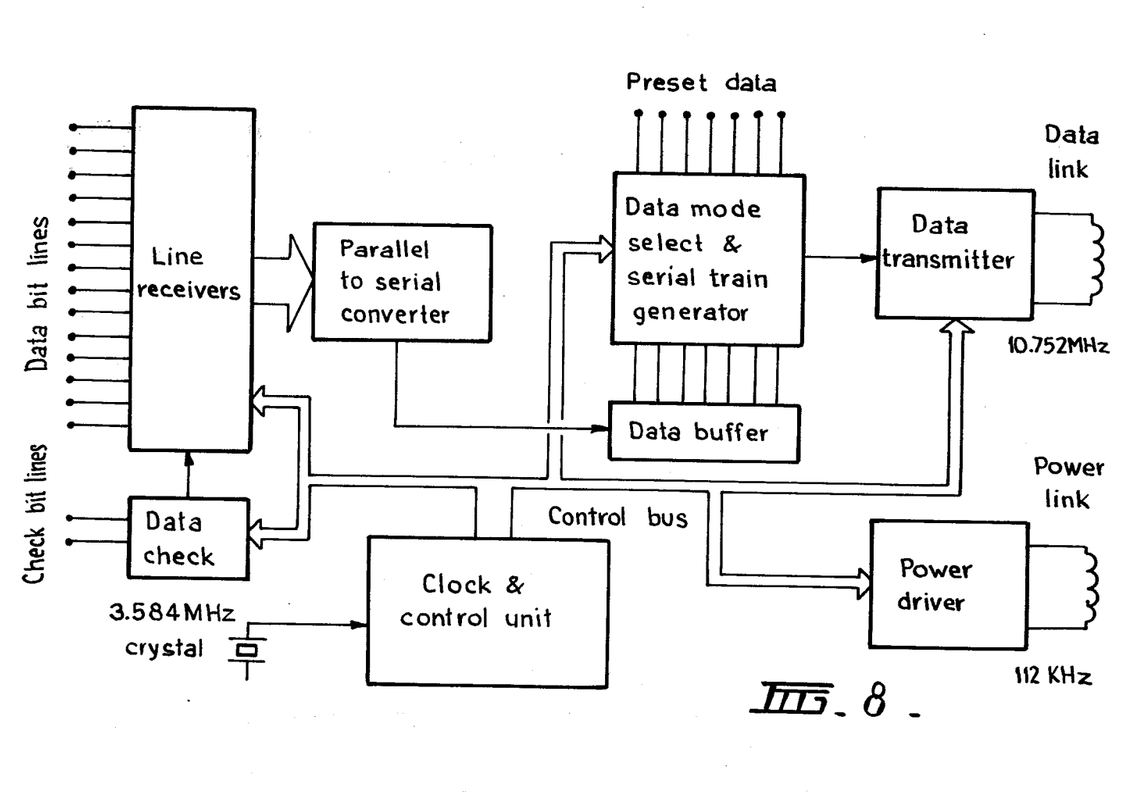
FIG. 8 is a block diagram of the transmitter.

We have, in this form of prosthesis, adopted a stimulus current from each channel being variable from 70 $\mu A$ to a maximum of approximately 1 mA in fifteen 70 $\mu A$ steps. This arrangement provides less than or equal to 6 dB increments in intensity for levels above 70 $\mu A$. The stimulus time format consists of basic 1 ms intervals or frames which are equal to the period of an external time reference. During each frame, control information for each channel is transferred to the receiver stimulator. Each frame is sub-divided into eight 125 $\mu s$ phase periods. The stimulation cycle may be initiated at the start of any phase period, except that any channel can only be stimulated once during any frame. Thus the maximum steady state frequency of stimulation for each channel is 1 KHz. The phase control parameter will allow variations in the temporal pattern of firing of different neural populations excited by the field of each electrode located along the length of the cochlea. Referring to FIG. 8, the stimulus data corresponding to the fifteen channels is presented to transmitter line receivers by a source which develops this from an audio signal, the data being presented in the form of eight 16 bit words loaded, as previously indicated, at the frame rate of 1 KHz. Each word, with the exception of the last, contains data for two channels and two check bits. The last word contains data for one channel only. The eight data words are converted to serial format and stored in the data buffer until required by the serial train generator. The loading of the data words can be formed in approximately 50 $\mu s$ and the remaining 950 $\mu s$ before the next data transfer are used to ensure that continuous transfer of data from auxiliary storage units to the transmitter can be maintained.

The clock and control units generates all timing and control information for the data loading, multiplexing and power/data transmission. All clocks are derived from a stable 3.584 MHz crystal.

The output of the data buffer comprises groups of seven bit words, which correspond with each channel, which words are loaded in parallel into the data mode selector and serial train generator. After loading each word is clocked out serially by the 112 KHz bit clock to finally modulate the data transmitter stage the output of which is a pulse-modulated high frequency carrier signal.

Figure 9:
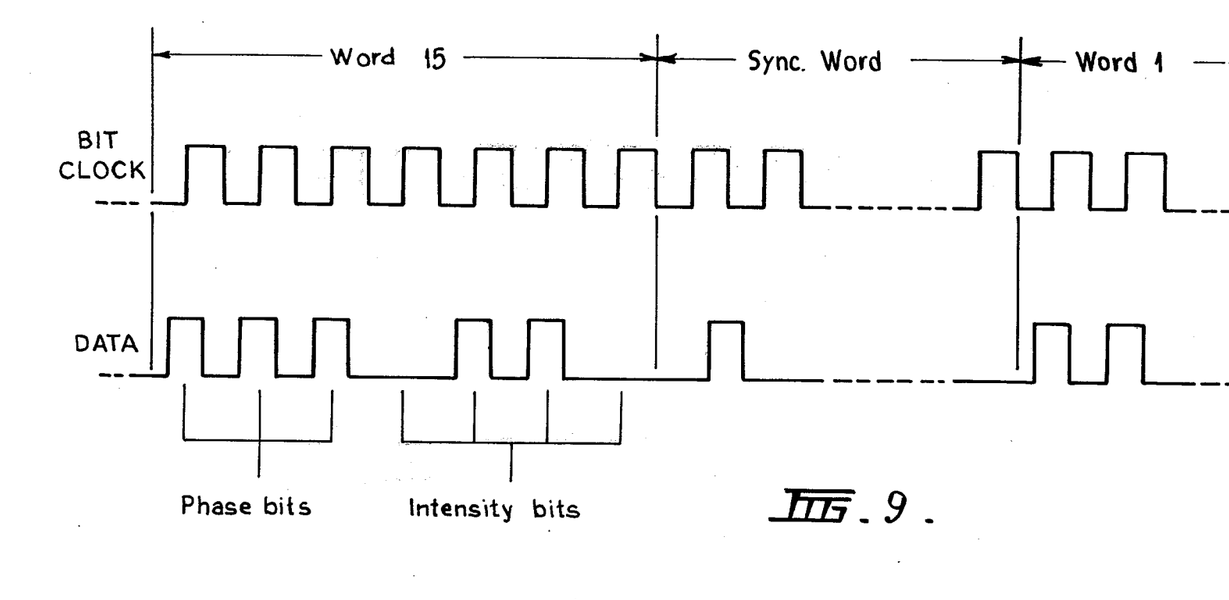
FIG. 9 is a timing diagram of a transmitter serial data train.
Figure 10:
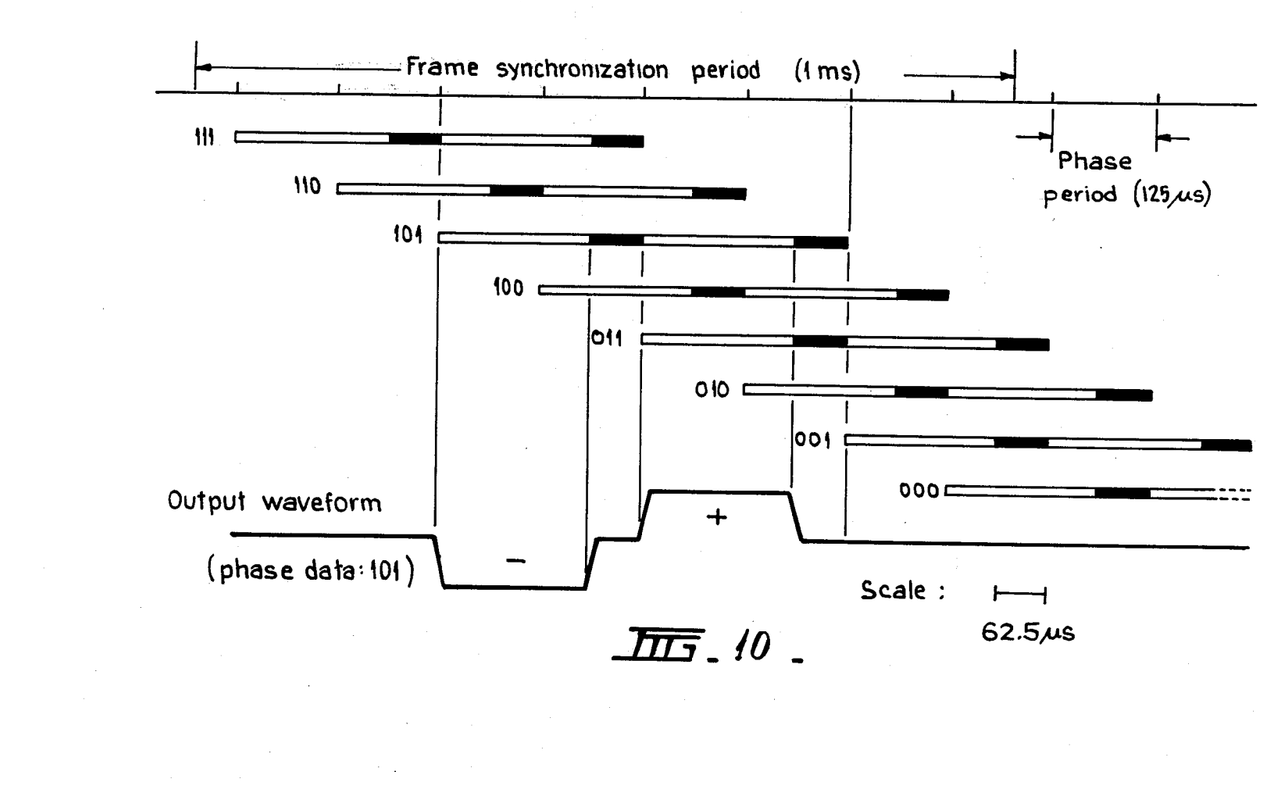
FIG. 10 is a timing diagram of the stimulus time format.

The output serial data train, a typical segment of which is shown in FIG. 9, comprises the 15 7 bit words corresponding to fifteen possible channels. Following the last word is a frame synchronising word which has a duration time equal to that of the channel word. Three of the data bits in any word in a frame are phase control bits which determine when stimulation is to be initiated for the corresponding channel during the following frame period and examination of FIG. 10 shows when stimulation is to be initiated for a channel during the following frame period. The remaining four bits in each word are intensity control bits and these determine, as previously indicated, the stimulus level for the channel during the next frame period.

The data and power links are, as previously indicated at 10.752 MHz and 112 KHz respectively. These take into consideration the power absorption of tissues at high frequencies, which as previously indicated was the major reason for adopting two carriers rather than the single carrier of the previous embodiment and they also minimise the cross talk between links. The links use two pairs of coils whose design is such that the coupling efficiency, misalignment tolerance (both axial and lateral) and minimisation from interference both from external radiation and by self radiation is optimized. The coils are constructed in the form of a flat disc or pancake configuration with the data coil being placed concentrically and co-planer with the power coil.

Figure 11:
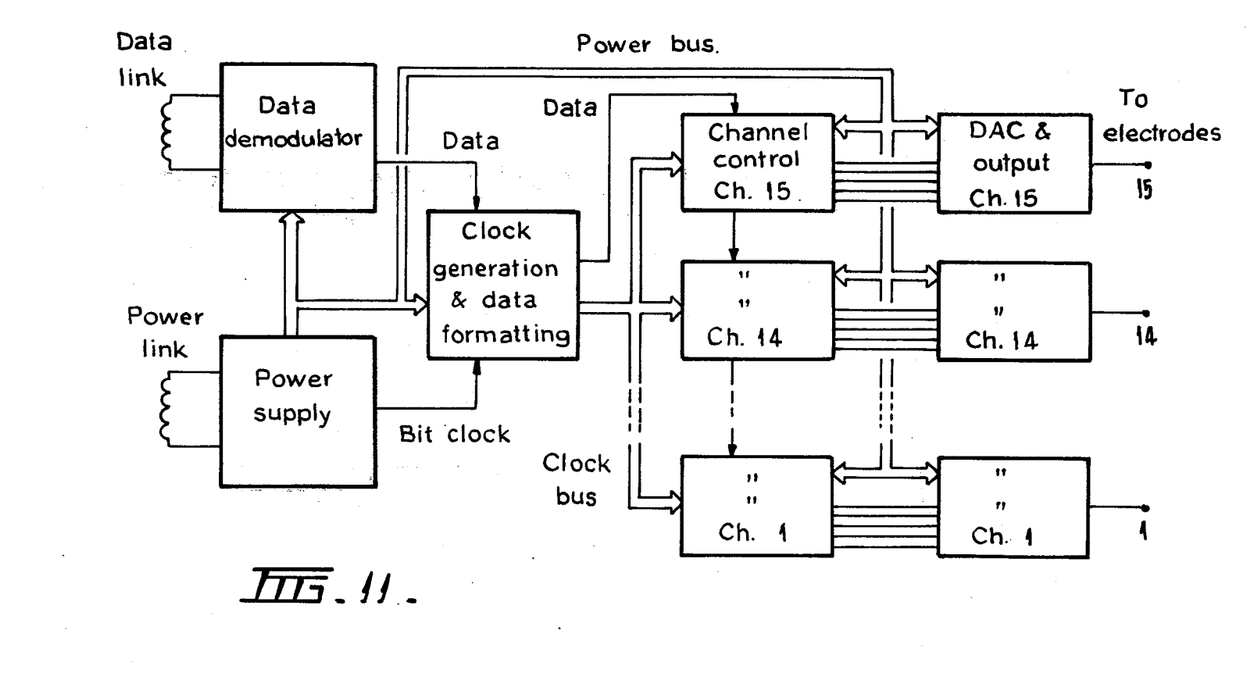
FIG. 11 is a block diagram of the receiver stimulator unit.

FIG. 11 is a block diagram of the receiver-stimulator unit. Both the power and data link signals are received by tuned circuits, to minimise interference from external radio frequency sources. The two supply rails, +7.5 V and −7.5 V, with reference to the implant ground, and are derived from the 112 KHz power link using bridge rectification and series pass regulation. These voltage levels also represent the two logic levels used in the digital circuitry, minimising the number of common bus lines. The bit clock is also derived from the unrectified power signal input. Two reference levels are required by the bi-phasic current output generators are derived from the supply rails. The pulsed radio frequency data signals are demodulated using an active detector.

The data train and bit clock are inputs to the clock generation and data formation stage. The outputs of this stage are common clock bus lines comprising the five clock and control lines necessary for timing control of the channel control stages and the serial data train. The control stage performs dual functions digitally de-multiplexing the serial train and decoding this data so that independent control over phase and intensity parameters may be effected for each channel. The serial data is clocked through the channel control stages in synchronism with the bit clock and is stored at the end of the frame period. This information is used to control the stimulus which is initiated during the following frame period.

The three phase bits for each channel preset a binary counter which is incremented by a clock with a period of 125 μs equal to the phase period. When the counter reaches a predetermined number the stimulation cycle is initiated and the four intensity bits are gated through the corresponding digital to analog converter (DAC) and the output stage for the particular channel. The voltage from the digital to analog converter drives a voltage-controlled bi-phasic current source.

A typical wave form is shown in FIG. 10 for the phase bit data 101. It should be noted that there is a period of 62.5 μs following each phase of the stimulus which allows the output current to return to zero. Without these intervals the effective band width limitations of the particular analog circuitry employed in this stage would produce asymmetries in the current wave form and corresponding charge imbalance.

When an electrode is not stimulated, it is electrically isolated from the circuitry. This isolation can also ensure that excessive stimulation can be prevented for a particular channel should a fault develop in the corresponding analog circuitry.

We previously indicated that the use of bi-phasic currents restricts the loss of metal from the electrodes and we also indicated that where the current is initially negative-going, this provides the least quantity of electrode loss.

Notwithstanding this, we may on occasions prefer to have adjacent channels having their initial phase alternating as this tends to counteract the effect of one channel against the other and thus provides a sharpening effect so that the stimulation is positively applied to the required place in the cochlea and does not tend to spread widely.

If this is to be done it is simply necessary that provision is made to invert the signal at each second channel of stimulation.

The same result can be achieved by a phase displacement between adjacent signals, although this is not, generally, as satisfactory.

Although the prosthesis of the present invention relates particularly to audio prostheses and although we have indicated particular limiting factors, such as forms of circuit and number of channels, it is to be understood that the invention can be used with other prostheses where signals need to be provided to neural endings and also the particular arrangement and number of channels can be varied widely and this may be most relevant as micro electronic techniques are varied.

We claim:

1. An aural prosthesis system comprising:
    a first part adapted to be located exteriorally of the body to transmit a data signal and a second part adapted to be located within the body to receive said data signal,
    said data signal comprising a plurality of sequential frames of an audio signal,
    each of said frames having a set of channel signals,
    each member of said set of channel signals including a first portion indicative of the channel signal intensity and a second portion indicative of the channel signal timing within the associated frame,
    a transmitter in said first part for transmitting said frames of said data signal as a series of sets of channel signals,
    a receiver in said second part for receiving the signal transmitted by said transmitter,
    first storage means in said second part for storing each member of a set of channel signals as it is received,
    loading means to load said sets of channel signals into said first storage means,
    second storage means in said second part to store each member of a set of channel signals,
    a plurality of electrodes adapted to be coupled to stimulate aural nerve endings, and
    coupling means to couple each member of the set of channel signals in said second storage means to a separate one of said electrodes, said first portion of each said members of said set determining the intensity of stimulation to be applied by the associated electrode and said second portion of each of said members of said set determining the time within the associated frame in which that stimulation is initiated by said associated electrode,
    said coupling means coupling the channel signals of a frame from said second storage means to said electrodes while said loading means is loading the set of channel signals from the next successive frame into said first storage means.

2. The prosthesis of claim 1 further comprising: a transmitter encoding means to convert each of said sets of channel signals constituting a frame from a parallel format to a serial format within the time span of said frame, each of said sets of channel signals in serial format being adapted for transmission, and
    receiver decoding means to convert each of said sets of channel signals from a serial format to a parallel format thereby reconstituting each frame of said data signal.

3. The prosthesis of claims 1 or 2 wherein each of said frames of said data signal includes a synchronization channel having a synchronization signal.

4. The prosthesis of claims 1 or 2 wherein the number of channels per frame is between seven and sixteen.

5. The prosthesis of claim 3 wherein the number of channels per frame is between seven and sixteen.

* * * * *